United States Patent [19]

Rydell et al.

[11] Patent Number: 4,806,182
[45] Date of Patent: Feb. 21, 1989

[54] METHOD OF BONDING A HUB TO A TEFLON-LINED CATHETER BODY

[75] Inventors: Mark A. Rydell, Excelsior; Rick L. Shockey, Roseville, both of Minn.

[73] Assignee: Schneider-Shiley (U.S.A.) Inc., Minneapolis, Minn.

[21] Appl. No.: 787,736

[22] Filed: Oct. 15, 1985

[51] Int. Cl.⁴ .............................................. B32B 31/28
[52] U.S. Cl. ................................. 156/211; 156/212; 156/214; 156/245; 156/294; 156/303.1; 264/127; 264/322
[58] Field of Search ..................... 128/348.1; 264/320, 264/322, 127; 156/196, 204, 211–212, 214, 218, 293–294, 303.1, 245

[56] References Cited

U.S. PATENT DOCUMENTS

| 2,284,761 | 6/1942 | Nathan . |
| 2,341,953 | 2/1944 | Scott . |
| 2,415,472 | 2/1947 | Dorman . |
| 3,192,612 | 7/1965 | Elliott et al. . |
| 3,266,821 | 8/1966 | Safford . |
| 3,307,860 | 3/1967 | Blount et al. . |
| 3,409,919 | 11/1968 | Carpenter . |
| 3,563,573 | 2/1971 | Crompton et al. . |
| 3,720,210 | 3/1973 | Diettrich . |
| 4,052,990 | 10/1977 | Dodgson . |
| 4,064,619 | 12/1977 | Echols et al. . |
| 4,354,495 | 10/1982 | Bodicky . |
| 4,391,029 | 7/1983 | Czuba et al. . |
| 4,523,968 | 6/1985 | McCool ............................... 156/294 |
| 4,551,292 | 11/1985 | Fletcher ............................... 264/320 |

*Primary Examiner*—Merrell C. Cashion, Jr.
*Attorney, Agent, or Firm*—Orrin M. Haugen; Thomas J. Nikolai

[57] ABSTRACT

A method of attaching a plastic hub member to the proximal end of a Teflon-lined thermoplastic tubular catheter so as to prevent delamination of the Teflon lining at the site of the attachment. The thermoplastic outer layer of the tubular catheter is removed in a grinding operation for a predetermined distance from the proximal end of the tube to expose a short length of the Teflon lining. Next, a spinning forming tool is forced against the proximal end of the tubular catheter causing the exposed Teflon lining to be rolled back over the outer surface of the thermoplastic tube. Next, the proximal end of the catheter is inserted into the bore of the hub and because the Teflon layer has been rolled over the end portion of the tubular catheter, it is trapped against an internal flange formed in the catheter hub when the hub is adhesively bonded to the exterior of the thermoplastic layer and prevented from delaminating and possibly occluding the lumen of the catheter.

2 Claims, 1 Drawing Sheet

METHOD OF BONDING A HUB TO A TEFLON-LINED CATHETER BODY

BACKGROUND OF THE INVENTION

I. Field of the Invention:

This invention relates generally a method of fabricating guide catheters, and more particularly to a method for securing the proximal hub to the catheter body without causing delamination of a Teflon lining of the catheter's lumen.

II. Discussion of the Prior Art:

A guide catheter comprises an elongated tubular member which may be inserted through an incision and routed through a vein or artery to a desired site, and then an angiography catheter or an angioplasty catheter of a smaller cross-sectional dimension may be routed through the guide catheter to the location where a dye or other medicament is to be injected or where an angioplasty procedure is to be carried out on a stenotic lesion. To facilitate the movement of the angiography catheter or the angioplasty catheter within the lumen of the guide catheter, it has been found convenient to line the lumen of the guide catheter with a thin Teflon layer because of the low coefficient of friction possessed by the Teflon material. The guide catheter itself typically comprises an elongated tube formed from a suitable thermoplastic material, such as polyethylene, and which may have reinforcing braid incorporated within the side walls and which is disposed about the thin Teflon liner. The hub may be a molded plastic part which has a central bore formed longitudinally therethrough and terminating internally in a counterbore of a lesser diameter extending inwardly from the distal end thereof and terminating in an annular shoulder. The diameter of the counterbore is only slightly larger than the outside diameter of the catheter body stock to which it is to be attached.

In the past, serious problems were encountered when an attempt was made to bond the hub to the proximal end of the catheter body stock. Specifically, the Teflon lining, because of its unique properties, is difficult to adhesively bond to the inner walls of the braid-reinforced polyethylene catheter body. Thus, there has been a tendency in the prior art for the Teflon lining to delaminate to the extent that it would block the lumen of the guide catheter. Thus, while the plastic hub can readily be bonded to the thermoplastic exterior of the catheter body stock, it has been necessary to devise a way for preventing the delamination of the Teflon liner covering the lumen of the thermoplastic tubular catheter.

The Diettrich U.S. Pat. No. 3,720,210, the Bodicky U.S. Pat. No. 4,354,495 and the Czuba et al U.S. Pat. No. 4,391,029 each describe ways of securing a molded plastic hub to the proximal end of a catheter body. In the Diettrich patent, the catheter body itself is made from polytetrafluoroethylene (Teflon) and is provided with an integral flange at one end and an additional outer tubular member or sleeve of a different plastic material, and the tube end and sleeve are insert molded in a hub member. Typical guide catheters, however, cannot be fabricated from a Teflon material because it is too rigid and inflexible if of a thickness to serve as the catheter body stock itself. It is for this reason that a stainless steel braid reinforced plastic with a Teflon lining to provide a low friction internal surface has worked so well. The flexibility and torque characteristics of the resulting catheter are dictated primarily by the outer plastic and the embedded blade while the Teflon lining is sufficiently thin as not to seriously increase the rigidity of the resulting catheter.

One drawback to this catheter construction has been the tendency of the thin Teflon lining to delaminate from the surrounding catheter body stock. The insertion of various working catheters through the lumen of the guide catheter and/or the introduction of fluids through the guide catheter has caused the Teflon lining to, at times, peel away from the surrounding tubular walls of the catheter's body stock. The present invention describes a method for bonding a hub to a Teflon-lined catheter in such a fashion that this delamination is prevented.

SUMMARY OF THE INVENTION

In accordance with the present invention, a continuous length of Teflon-lined, stainless steel braid reinforced thermoplastic tubing is cut to a desired length for a guide catheter and the end which is to be the proximal end of the catheter is placed in a centerless grinder which is used to remove the thermoplastic and the stainless steel braid over a short predetermined length of the catheter, thus exposing the Teflon layer. Next, the proximal end of this piece of tubing is pressed against a spinning forming tool which serves to roll the exposed Teflon layer back over the ground end of the catheter so that when that end is now inserted in the hub's counterbore and pressed against the annular flange formed therein, the rolled-back Teflon layer is trapped and locked in place when the hub is bonded onto the catheter body.

OBJECTS

It is a principal object of the present invention to provide a new and improved guide catheter.

Another object of the invention is to provide a method of bonding a hub to the proximal end of a Teflon-lined guide catheter in such a fashion that the Teflon lining is held in place and precluded from delaminating.

Yet another object of the invention is to provide an improved method of manufacturing guide catheters whereby the yield of acceptable catheters is markedly increased.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
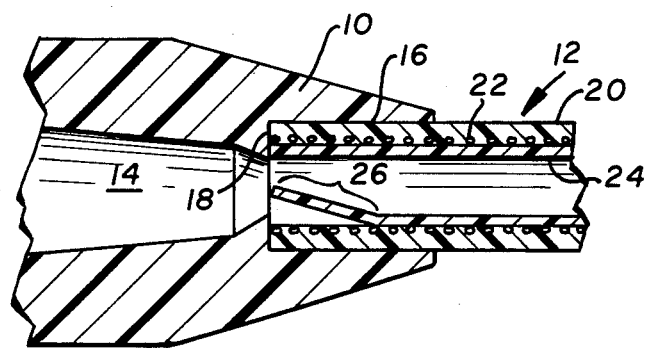
FIG. 1 is a cross-sectional view of the hub-end portion of a prior art catheter illustrating the delamination problem solved by the method of the present invention.

Referring to FIG. 1, there is shown a portion of the proximal end of a guide catheter made in accordance with prior art methods. There is shown in cross-section, a molded plastic hub 10 which has been bonded to the proximal end of a guide catheter 12. The hub 10 includes a tapered bore 14 which terminates in a generally cylindrical counterbore 16 into which the proximal end of the catheter 12 is fitted. In that the counterbore 16 is of a slightly larger diameter than the tapered bore 14, an annular flange 18 is created at the intersection of the bore 14 and the counterbore 16. The proximal end of the catheter is inserted in the counterbore 16 and pushed up against the flange 18 before being chemically bonded to the hub.

As shown in FIG. 1, the guide catheter 12 includes a thermoplastic tubular member 20 having a stainless steel braid 22 embedded in the wall thereof and an inner tubular layer 24 of Teflon material adhesively or chemically bonded to the interior wall surface of the outer thermoplastic tubular member 20.

Because Teflon is difficult to bond to many thermoplastic materials, such as polyurethane, there is often a tendency for the Teflon layer 24 to delaminate from the interior wall of the tube 20 as indicated by the bracketed zone 26. In some instances, the delamination becomes so great that the central lumen of the catheter 12 becomes blocked or occluded. It is the purpose of the method of the present invention to obviate this delamination problem.

Figure 2:
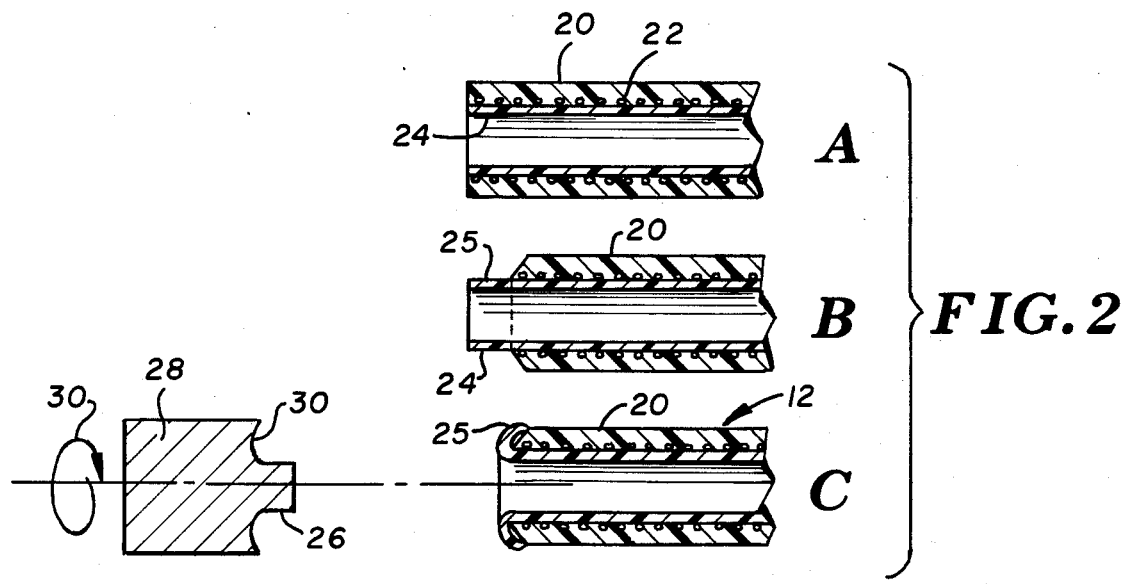
FIGS. 2A through 2C illustrate the steps of the method for obviating the delamination problem.

Referring to FIG. 2A, there is shown a cross-section of a piece of catheter body stock after it has been cut to length. As in FIG. 1, it comprises an outer tube of a suitable thermoplastic material such as polyurethane 20 into which is embedded a stainless steel braid 22. Again, the interior wall of this thermoplastic tube 20 is covered by a Teflon lining layer 24.

With reference to FIG. 2B, the next step in the process is to grind away a short predetermined length of the polyurethane and braid from the end portion of the catheter body stock of FIG. 2A so as to leave exposed the Teflon layer 24. It has been found that for most catheters, removal of approximately 1/16th of an inch of the stainless steel braid reinforced layer 20 produces effective results.

Following the grinding step in which the outer covering 20 is removed, the proximal end of the catheter body stock 12 is fitted over the tapered end 26 of a forming tool 28 which is made to spin in a chuck as indicated by the arrow 30. The tapered portion 26 of the forming member 28 terminates in a cup-shaped annular zone 30 and, when the catheter body of FIG. 2B is forced against the cup-like recess 30, the end portion 25 of the Teflon layer 24 is rolled back over the ground-off end edge of the outer tubular member 20.

Figure 3:
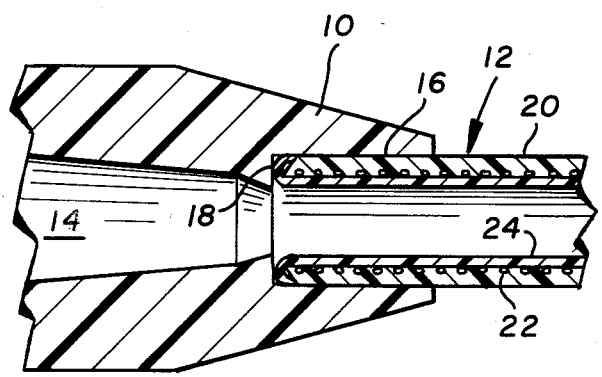
FIG. 3 is a cross-sectional view of the hub portion of a catheter made in accordance with the method of the present invention.

Next, as shown in FIG. 3, the proximal end of the tubular catheter body 12 is fitted into the counterbore 16 of the hub 10 and pushed into that counterbore until the rolled-over end portion 25 of the Teflon lining abuts the face of the annular flange 18. Now, when the hub is bonded onto the exterior surface of the thermoplastic layer 20, the rolled-back Teflon layer is trapped and cannot unroll to the point where delamination can again occur.

Thus, there has been shown and described a method for manufacturing an improved catheter of the type having a Teflon lining. More specifically, the method of the present invention precludes delamination of that Teflon lining and ensures a greater yield of high quality catheter products.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A method of attaching a plastic hub to the proximal end of an elongated flexible tubular catheter of the type having an outer thermoplastic tube whose lumen is lined with a Teflon layer comprising the steps of:
   (a) cutting a predetermined length of the Teflon-lined tubing from a continuous length of such materials;
   (b) removing the outer thermoplastic layer from a short end portion of said catheter body to expose the underlying Teflon layer in said short end portion;
   (c) rolling the exposed portion of said Teflon layer back over the end of said thermoplastic tube; and
   (d) inserting said end portion of said catheter body into a bore formed in said hub such that the rolled end portion of the Teflon layer is trapped and precluded from unrolling; and
   (e) bonding said catheter body to the interior wall of said counterbore in said hub.

2. The method as in claim 1 wherein said step of rolling said Teflon layer back over the end portion of said flexible thermoplastic tubular member comprises:
   (a) the step of rotating a symmetrical forming tool having a predetermined annular profile formed in the periphery thereof; and
   (b) advancing the proximal end of said catheter body with the exposed Teflon layer against said profile.

* * * * *